US012171409B2

(12) United States Patent
Lesch et al.

(10) Patent No.: US 12,171,409 B2
(45) Date of Patent: *Dec. 24, 2024

(54) WIRELESS ENDOSCOPE

(71) Applicant: Entellus Medical, Inc., Plymouth, MN (US)

(72) Inventors: Paul Lesch, Lino Lakes, MN (US); Cliff Dowdy, Montrose, CO (US)

(73) Assignee: Stryker Corporation, Portage, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/369,589

(22) Filed: Sep. 18, 2023

(65) Prior Publication Data

US 2024/0041308 A1    Feb. 8, 2024

Related U.S. Application Data

(63) Continuation of application No. 17/510,776, filed on Oct. 26, 2021, now Pat. No. 11,779,199, which is a
(Continued)

(51) Int. Cl.
*A61B 1/00* (2006.01)
*A61B 1/04* (2006.01)
(Continued)

(52) U.S. Cl.
CPC .......... *A61B 1/045* (2013.01); *A61B 1/00006* (2013.01); *A61B 1/00009* (2013.01);
(Continued)

(58) Field of Classification Search
CPC . A61B 1/045; A61B 1/00006; A61B 1/00009; A61B 1/00016; A61B 1/00045;
(Continued)

(56) References Cited

U.S. PATENT DOCUMENTS

D326,714 S    6/1992  Funakoshi
6,554,765 B1  4/2003  Yarush
(Continued)

FOREIGN PATENT DOCUMENTS

CN    10405806      5/2015
JP    2-289222 A   11/1990
(Continued)

OTHER PUBLICATIONS

Wireless Endoscope Camera. May 6, 2020, fireflyglobal.com/de1250-wireless-endoscope-camera/. (Year: 2015).
(Continued)

*Primary Examiner* — Howard D Brown, Jr.
(74) *Attorney, Agent, or Firm* — McDonnell Boehnen Hulbert & Berghoff LLP

(57) ABSTRACT

Disclosed embodiments relate to an endoscopic camera and methods for operating the camera. In one embodiment, the endoscopic camera includes a grip region to facilitate holding by a user. The camera may also include a mechanism for correcting improperly exposed video signals by modulating illumination parameters.

20 Claims, 9 Drawing Sheets

Related U.S. Application Data continuation of application No. 16/330,708, filed as application No. PCT/US2017/017199 on Feb. 9, 2017, now Pat. No. 11,191,421.

(60) Provisional application No. 62/385,892, filed on Sep. 9, 2016.

(51) Int. Cl.
| | |
|---|---|
| *A61B 1/045* | (2006.01) |
| *A61B 1/06* | (2006.01) |
| *H04N 23/54* | (2023.01) |
| *H04N 23/67* | (2023.01) |
| *H04N 23/71* | (2023.01) |
| *H04N 23/74* | (2023.01) |
| *H04N 23/50* | (2023.01) |

(52) U.S. Cl.
CPC ...... *A61B 1/00016* (2013.01); *A61B 1/00045* (2013.01); *A61B 1/00066* (2013.01); *A61B 1/042* (2013.01); *A61B 1/0655* (2022.02); *A61B 1/0684* (2013.01); *H04N 23/54* (2023.01); *H04N 23/671* (2023.01); *H04N 23/71* (2023.01); *H04N 23/74* (2023.01); *H04N 23/555* (2023.01)

(58) Field of Classification Search
CPC ... A61B 1/00066; A61B 1/042; A61B 1/0655; A61B 1/0684; A61B 1/00032; A61B 1/0669; H04N 23/54; H04N 23/671; H04N 23/71; H04N 23/74; H04N 23/555; H04N 23/56; H04N 23/51; H04N 23/65; H04N 23/661
IPC ........................................................ A61B 1/00
See application file for complete search history.

(56) References Cited

U.S. PATENT DOCUMENTS

| | | | |
|---|---|---|---|
| D548,328 S | 8/2007 | Fedenia | |
| D553,242 S | 10/2007 | Fedenia | |
| 7,520,876 B2 | 4/2009 | Ressemann et al. | |
| 7,678,099 B2 | 3/2010 | Ressemann et al. | |
| 7,842,062 B2 | 11/2010 | Keith et al. | |
| 7,879,061 B2 | 2/2011 | Keith et al. | |
| D635,257 S | 3/2011 | Ellman | |
| 7,918,871 B2 | 4/2011 | Truitt et al. | |
| D639,428 S | 6/2011 | Yasue | |
| 8,241,266 B2 | 8/2012 | Keith et al. | |
| 8,277,478 B2 | 10/2012 | Drontle et al. | |
| 8,282,667 B2 | 10/2012 | Drontle et al. | |
| 8,348,969 B2 | 1/2013 | Keith et al. | |
| 8,568,439 B2 | 10/2013 | Keith et al. | |
| 8,585,728 B2 | 11/2013 | Keith et al. | |
| 8,585,729 B2 | 11/2013 | Keith et al. | |
| 8,623,043 B1 | 1/2014 | Keith et al. | |
| 8,657,846 B2 | 2/2014 | Keith et al. | |
| 8,801,670 B2 | 8/2014 | Drontle et al. | |
| 8,834,513 B2 | 9/2014 | Hanson et al. | |
| 8,882,795 B2 | 11/2014 | Drontle et al. | |
| 8,888,686 B2 | 11/2014 | Drontle et al. | |
| 8,915,938 B2 | 12/2014 | Keith et al. | |
| 9,002,285 B2* | 4/2015 | Hasegawa | H04W 72/02 455/66.1 |
| 9,005,284 B2 | 4/2015 | Ressemann | |
| 9,101,739 B2 | 8/2015 | Lesch, Jr. et al. | |
| 9,192,748 B2 | 11/2015 | Ressemann et al. | |
| 9,278,199 B2 | 3/2016 | Keith et al. | |
| 9,282,986 B2 | 3/2016 | Hanson et al. | |
| 9,283,360 B2 | 3/2016 | Lesch et al. | |
| D753,296 S | 4/2016 | Gill | |
| 9,320,876 B2 | 4/2016 | Ressemann et al. | |
| 9,333,327 B2 | 5/2016 | Setliff, III et al. | |
| 9,339,637 B2 | 5/2016 | Drontle et al. | |
| 9,370,650 B2 | 6/2016 | Hanson et al. | |
| 9,433,343 B2 | 9/2016 | Drontle et al. | |
| 9,440,049 B2 | 9/2016 | Drontle et al. | |
| D771,252 S | 11/2016 | Osada | |
| 9,486,614 B2 | 11/2016 | Drontle et al. | |
| D776,811 S | 1/2017 | Ogura | |
| 9,550,049 B2 | 1/2017 | Hanson et al. | |
| D782,039 S | 3/2017 | Teufel | |
| D790,697 S | 6/2017 | Bresco | |
| 9,694,167 B2 | 7/2017 | Keith et al. | |
| 9,700,705 B2 | 7/2017 | Lesch, Jr. et al. | |
| D793,554 S | 8/2017 | Shimobayashi | |
| 9,775,975 B2 | 10/2017 | Ressemann et al. | |
| D823,463 S | 7/2018 | Shaw | |
| 10,022,525 B2 | 7/2018 | Hanson et al. | |
| 10,029,069 B2 | 7/2018 | Keith et al. | |
| 10,842,557 B2* | 11/2020 | Sharma | A61B 5/1076 |
| 10,986,181 B2 | 4/2021 | Klose et al. | |
| 11,191,421 B2* | 12/2021 | Lesch | H04N 23/65 |
| 11,779,199 B2* | 10/2023 | Lesch | A61B 1/042 348/69 |
| 2001/0015754 A1 | 8/2001 | Nakashima et al. | |
| 2008/0172033 A1 | 7/2008 | Keith et al. | |
| 2009/0247828 A1 | 10/2009 | Watanabe | |
| 2011/0193949 A1 | 8/2011 | Nambakam et al. | |
| 2011/0208004 A1 | 8/2011 | Feingold et al. | |
| 2013/0204085 A1* | 8/2013 | Alexander | A61B 1/00158 600/101 |
| 2013/0324794 A1 | 12/2013 | Cover et al. | |
| 2014/0052004 A1 | 5/2014 | D'Alfonso et al. | |
| 2014/0139130 A1 | 5/2014 | Upton | |
| 2014/0221740 A1* | 8/2014 | Kawula | A61B 1/00016 600/109 |
| 2015/0116470 A1* | 4/2015 | Ovod | A61B 1/042 348/68 |
| 2015/0126990 A1* | 5/2015 | Sharma | A61B 17/3415 606/30 |
| 2016/0151614 A1 | 6/2016 | Ressemann et al. | |
| 2016/0166814 A1 | 6/2016 | Lesch et al. | |
| 2016/0354140 A1* | 12/2016 | Sharma | A61B 90/39 |
| 2016/0367286 A1 | 12/2016 | Drontle et al. | |
| 2017/0007282 A1 | 1/2017 | Drontle | |
| 2017/0028112 A1 | 2/2017 | Drontle et al. | |
| 2017/0050001 A1 | 2/2017 | Drontle et al. | |
| 2017/0113027 A1 | 4/2017 | Drontle et al. | |
| 2017/0368319 A1 | 12/2017 | Lesch, Jr. et al. | |
| 2018/0008806 A1 | 1/2018 | Ressemann et al. | |

FOREIGN PATENT DOCUMENTS

| | | |
|---|---|---|
| JP | 2001-286440 | 10/2001 |
| WO | 2014/028758 A1 | 2/2014 |

OTHER PUBLICATIONS

Anonymous: Wireless Endoscope Camera: Firefly Global, Aug. 14, 2016 (Aug. 14, 2016). XP055595612 Retrieved from the Internet: URL:https:jjweb.archive.orgjweb/20160814133954/http://fireflyglobal.comjde 1250-wireless-endoscope-camera/ [retrieved on Jun. 11, 2019].

Anonymous: "Wireless Endoscope Camera image", Aug. 14, 2016 (Aug. 14, 2016). XP055595626. Retrieved from the Internet: URL:https:jweb.archive.orgjweb/20160814133954/http://fireflyglobal.comjde1250-wireless-endoscope-camera//#DE500jump [retrieved on Jun. 11, 2019].

Anonymous: "Firefly Endoscopic Camera Image with user hand", Aug. 14, 2016 (Aug. 14, 2016). XP055595636. Retrieved from the Internet: URL:https:jweb.archive.orgjweb/20160814133954/http://fireflyglobal.comjde 1250-wireless-endoscope-camera/ [retrieved on Jun. 11, 2019].

Anonymous: "Firefly Endoscopic Camera Image Front View", Aug. 14, 2016 (Aug. 14, 2016). XP055595799. Retrieved from the Internet: URL:https:jjweb.archive.orgjweb/20160814133954/http://fireflyglobal.comjde1250-wireless-endoscope-camera/ [retrieved on Jun. 12, 2019].

(56) References Cited

OTHER PUBLICATIONS

PCT International Preliminary Report on Patentability (Chapter I of the Patent Cooperation Treaty) for PCT/US2017/017199, Applicant: The Regents of the University of California, Form PCT/IB/326 and 373, dated Mar. 21, 2019 (8pages).
PCT International Search Report for PCT/US2017/017199, Applicant: Entellus Medical, Inc., Form PCT/ISA/210 and 220, dated Jun. 2, 2017 (5pages).
PCT Written Opinion of the International Search Authority for PCT/US2017/017199, Applicant: Entellus Medical, Inc., Form PCT/ISA/237, dated Jun. 2, 2017 (6pages).
Wireless Endoscope Camera, Firefly Global, http://fireflyglobal.com/de1250-wireless-endoscope-camera/, printed: Sep. 8, 2016 (4pages).
U.S. Appl. No. 29/577,198, filed Sep. 9, 2016, entitled: Endoscopic Camera; Inventor: Paul Lesch, (not yet published).

\* cited by examiner

WIRELESS ENDOSCOPE

CROSS-REFERENCE TO RELATED APPLICATIONS

This Application is a continuation of U.S. patent application Ser. No. 17/510,776, filed Oct. 26, 2021, which is a continuation of U.S. patent application Ser. No. 16/330,708 filed on Mar. 5, 2019, which claims priority to U.S. Provisional Patent Application No. 62/385,892 filed on Sep. 9, 2016, which are hereby incorporated by reference in their entirety. Priority is claimed pursuant to 35 U.S.C. § 119 and any other applicable statute.

BACKGROUND

The present disclosure relates generally to endoscopes and components thereof. Although existing endoscopes can be used to visualize a scene of interest during a procedure, there remains a need for new and improved designs. In particular, there remains a need for new systems, devices, and techniques that provide a more ergonomic user experience during endoscopy. There is also a need for systems, devices, and techniques that can reduce excess heat and power consumption of an endoscope. At the same time, there is also a need for systems, devices, and techniques that can offer these advantages without incorporating the same limitations as the existing art.

SUMMARY

In one aspect of the present disclosure, a method for visualizing a scene of interest using an endoscope involves advancing a distal end of an endoscope to a scene of interest, illuminating the scene of interest using an illumination source coupled to the endoscope, and capturing a video signal of the scene of interest using a camera coupled to the endoscope. The camera may have one or more video capture characteristics affecting exposure. The method may further include determining that the scene of interest is overexposed or underexposed in the video signal and changing the light output of the illumination source, while maintaining the same video capture characteristics affecting exposure, thereby correcting the overexposure or underexposure.

Examples of the video capture characteristics affecting exposure of the video signal include, but are not limited to, shutter speed, exposure time, and imaging sensor sensitivity to light. In some embodiments, the video capture characteristics may be set to maximize exposure. Optionally, the method may also involve wirelessly transmitting the video signal to a receiver coupled to a monitor. In some embodiments, the video signal may be uncompressed. In some embodiments, the camera and the light source are cordless, so that the endoscope is not attached to a separate light box via a cord.

In another aspect of the present disclosure, a method of gripping an endoscope involves gripping the endoscopic camera by placing a hand on a grip member at a first end of the camera. The transmitter of the camera can be located near a second end of the camera, opposite the first end, and the distance between the grip member and the transmitter can be at least 5 cm. The balance point of the camera and the endoscope, when they are coupled together, may be located at the grip member.

In some embodiments, the grip member may include a shoulder, and gripping the endoscopic camera may involve placing a part of the hand against or along the shoulder, thereby facilitating rotation of endoscopic camera. In some embodiments, the grip member may include a ledge extending from the grip member, and gripping the endoscopic camera may involve placing a part of the hand against or along the ledge, thereby facilitating desired distal or proximal motion of endoscopic camera. In some embodiments, the grip member may include an attachment collar, and gripping the endoscopic camera may involve gripping the attachment collar, thereby facilitating user control of the endoscopic camera. In some embodiments, the grip member may include an attachment collar, a shoulder, and a ledge extending from the grip member, and gripping the endoscopic camera may involve gripping the attachment collar, placing a part of the hand against the shoulder, and placing a part of the hand against the ledge, thereby facilitating control of the endoscopic camera.

In another aspect of the present disclosure, a wireless endoscopic camera may include a grip region, a ledge and a wireless transmitter. The grip region is located at a first end of the endoscopic camera and includes a face and an attachment collar extending from the face in a first direction perpendicular to the grip region. The attachment collar is adapted to couple the endoscopic camera to an endoscope. The ledge extends from the grip region in the first direction, below the attachment collar, and is configured to resist movement of the endoscopic camera in a user's hand. The first ledge may include a first concavity and a second concavity separated by a first convexity, where the first and second concavities are adapted to accommodate the user's fingers. The wireless transmitter may be located near a second end of the camera opposite the first end of the camera.

In some embodiments, a distance between the grip region and the wireless transmitter may be at least 5 centimeters. In some embodiments, a balance point of the camera, when attached to the endoscope, is located at the grip member. In some embodiments, the grip region may include two shoulders. The two shoulders may be configured to resist unwanted rotation of the endoscopic camera in the user's hand.

In yet another aspect of the present disclosure, a wireless endoscopic camera system may include an endoscopic camera as described above and a light source directly couplable to an endoscope and not requiring connection to a separate light box device. The system may also include a cable for connecting the light source to the endoscopic camera. In one embodiment, the light source is in the form of a cylindrical canister with a port for attaching to the endoscope.

These and other aspects and embodiments of the present disclosure are described in more detail below, in reference to the attached drawing figures.

DETAILED DESCRIPTION

Figure 1:
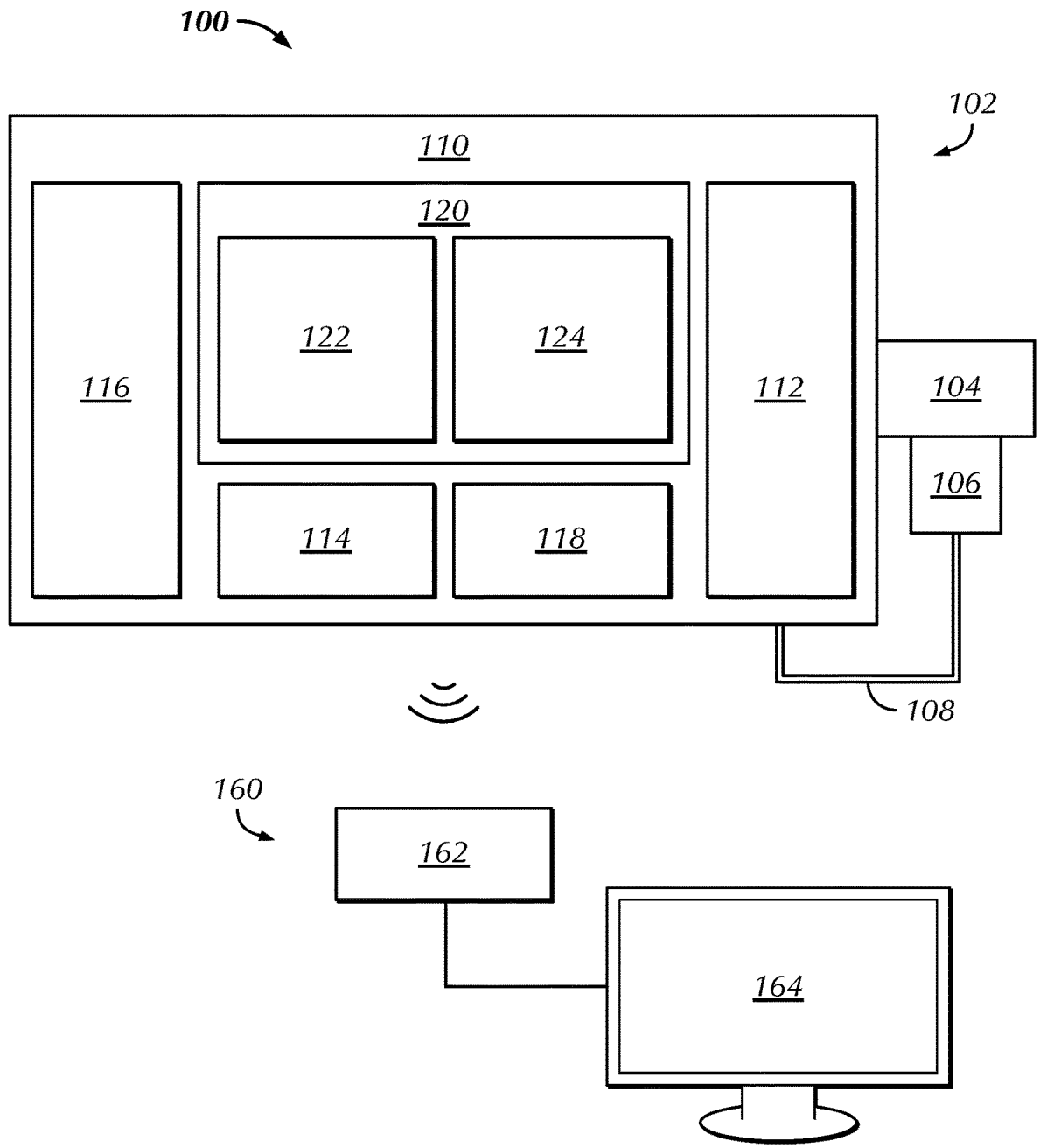
FIG. 1 is a block diagram of an endoscopic camera system, including a wireless endoscope and a viewing station, according to one embodiment.

Devices, systems, and methods for endoscopy are disclosed. Endoscopy can be used during medical procedures to visualize a scene of interest and aid a healthcare professional in conducting the procedure. For example, endoscopy can be used to facilitate positioning of a balloon dilation catheter during a procedure to treat sinusitis, such as described in U.S. Pat. No. 9,370,650, entitled "Method and Articles for Treating the Sinus System," which is hereby incorporated herein by reference for any and all purposes.

Proper visualization of a scene of interest during a procedure can be vitally important. Endoscopes having improved ergonomics can facilitate proper visualization and can contribute to improved patient outcomes. Because wires can limit user mobility, one way to improve ergonomics is to make the endoscope wireless, but the added weight and bulk from batteries and wireless transmitters can present their own ergonomic challenges.

Embodiments described herein are relevant to improving user control and ergonomics of an endoscope by providing an improved grip region, by which the user can control the device. Further, in some embodiments, the endoscope modulates illumination of the scene of interest to control exposure of the scene, thereby decreasing power consumption and heat output.

In one embodiment, an endoscopic camera includes a grip region having an attachment collar to which a scope can be coupled. The grip region further includes shoulders and a ledge having concavities. These features can provide points by which a user can grasp and manipulate the device to provide improved control. The grip region can be located a particular distance away from a wireless transmitter of the endoscopic camera.

In one embodiment, the endoscopic camera has camera settings that control exposure (e.g., exposure time and sensor gain). These settings can be kept at a relatively high level (e.g., tending to overexpose the captured images), and the endoscopic camera can modulate illumination provided by a light connected to the endoscope to correct for improper exposure. Because endoscopes are typically used inside a body cavity, the illumination provided by the endoscope is substantially the only source of illumination to the scene of interest. Therefore, controlling illumination can effectively correct exposure without needing to adjust camera exposure settings. In addition, by keeping camera exposure settings relatively high, the illumination output can be kept relatively low, which can reduce power draw from the light and heat generation. These improvements can allow for a decrease in battery size and lessen the need for heat sinks, thereby contributing to a lighter and less bulky endoscope.

The visual data captured by the endoscopic camera can be wirelessly transmitted to a receiver for display on a monitor. A user can view the image on the monitor to visualize the scene of interest. The parameters of the endoscopic camera, receiver, and monitor can be selected to reduce a delay between the visual data being generated by a camera sensor and the visual data being displayed at the monitor. For example, the visual data can be uncompressed data, thereby reducing the delay caused by compressing and uncompressing the data. The visual data can be transmitted with limited error correction and limited redundancy, without waiting for missing data and without breaking down large data into individual packets, thereby reducing overhead and latency. In one embodiment, for example, the data is transmitted using the uniform datagram protocol (UDP), rather than the transmission control protocol (TCP), to reduce latency.

FIG. 1 is a block diagram of one exemplary embodiment of an endoscopic visualization system 100, which includes a wireless endoscopic camera system 102 and a viewing station 160. In general, in this application, the phrase "endoscopic camera system" will refer to an endoscope attached to an endoscopic camera and a light source. However, in various embodiments an endoscopic camera system according to the present application may be provided as only an endoscopic camera, a coupler for attaching the camera to an endoscope, and a light source. In other embodiments, the coupler might not be included in the system. In other words, in some embodiments, an endoscopic camera system may not include the endoscope itself, as this may be provided or available as a separate component. The embodiment shown in FIG. 1 of endoscopic visualization system 100 is a more inclusive system, because it includes endoscopic camera system 102 and viewing station 160. System 100 can be used for visualizing scenes of interest during an endoscopic procedure, such as the examination of sinus passages and cavities. Endoscopic camera system 102 captures video, images and/or other data and transmits the information to viewing station 160 for display.

Endoscopic camera system 102 includes an endoscope 104, a light 106, a cable 108, and an endoscopic camera 110. Endoscope 104 guides light from a distal end of endoscope 104 near a scene of interest to a proximal end of endoscope 104, to provide a view for capture by endoscopic camera 110. Endoscope 104 includes a port for receiving illumination from light 106, which endoscope 104 uses to illuminate the scene of interest. In various embodiments, endoscope 104 may be flexible or rigid and may have any of a variety shapes and sizes. For example, endoscope 104 can take the form of a scope from the FocESS™ line of sinuscopes, provided by Entellus Medical™ of Plymouth, Minnesota. Because endoscopes are generally well known, and because endoscopic camera system 102 may, in various embodiments, be used with any suitable endoscope 104, this application will not describe endoscope 104 in further detail.

Light 106 is a source of illumination and can be coupled to endoscope 104. Light 106 can include light emitting diodes (LEDs) or other sources of illumination. Light 106 may include associated driver circuitry which is located in the endoscopic camera 110 or is external thereto. Light 106 can include its own power source or can receive power from an external source, such as endoscopic camera 110. For example, light 106 can be coupled to endoscopic camera 110 via cable 108. Light 106 can have adjustable illumination settings. For example, such illumination settings may be adjustable by a signal (e.g., a signal from endoscopic camera 110), by a control panel on light 106, or in another manner.

Endoscopic camera 110 captures a view (e.g., a view transmitted by endoscope 104) as video, images, or other data. Endoscopic camera 110 includes a camera 112, a battery 114, and a wireless transmitter 116.

Camera 112 is a portion of endoscopic camera 110 that converts visual information received from endoscope 104 into electrical information. Battery 114 is a power source for endoscopic camera 110 and can also power light 106. Battery 114 can be removable by the user or be integrated into endoscopic camera 110. Battery 114 can take various forms and can be rechargeable (e.g., battery 114 can be a rechargeable lithium-ion battery). Wireless transmitter 116 can transmit data from endoscopic camera 110 to a receiver. In some embodiments, endoscopic camera 110 can be configured to also wirelessly receive data.

Wireless transmitter 116 can be configured to communicate data over a variety of different protocols and may include associated hardware to transmit the data over a protocol. These protocols can include WirelessHD™, Bluetooth™, WiFi™, other protocols, and combinations thereof.

Endoscopic camera 110 further includes one or more computing components, including a processing unit 118 and a memory 120. Processing unit 118 can be implemented using one or more processors (e.g., CPUs) or other circuitry for performing processing tasks. Memory 120 may be implemented using any suitable electronically accessible memory, including but not limited to RAM, ROM, Flash, SSD, or hard drives.

Memory 120 includes executable instructions for adjusting illumination 122 and other executable instructions 124. Executable instructions for adjusting illumination 122 may include instructions executable by processing unit 118 for controlling illumination of the scene of interest by, for example, controlling power to light 106. Executable instructions for adjusting illumination 122 may include instructions for performing some of the steps described in relation to FIG. 11.

Other executable instructions 124 include other instructions for processing unit 118, including but not limited to instructions for white balancing data from camera 112, instructions for encoding data from camera 112, instructions for controlling wireless transmitter 116 (e.g., instructions for pairing wireless transmitter 116 with a receiver 162), instructions for controlling camera 112, and/or other instructions.

Viewing station 160 is a station for receiving and viewing data from endoscopic camera system 102. Viewing station 160 includes a receiver 162 for receiving data transmitted by wireless transmitter 116 of endoscopic camera system 102. Monitor 164 is a device for displaying, storing, and/or otherwise acting on the data received at receiver 162. In some embodiments, the receiver 162 may be physically separate from the monitor 164. Alternatively, the receiver 162 may be incorporated into the monitor 164.

Figure 2:
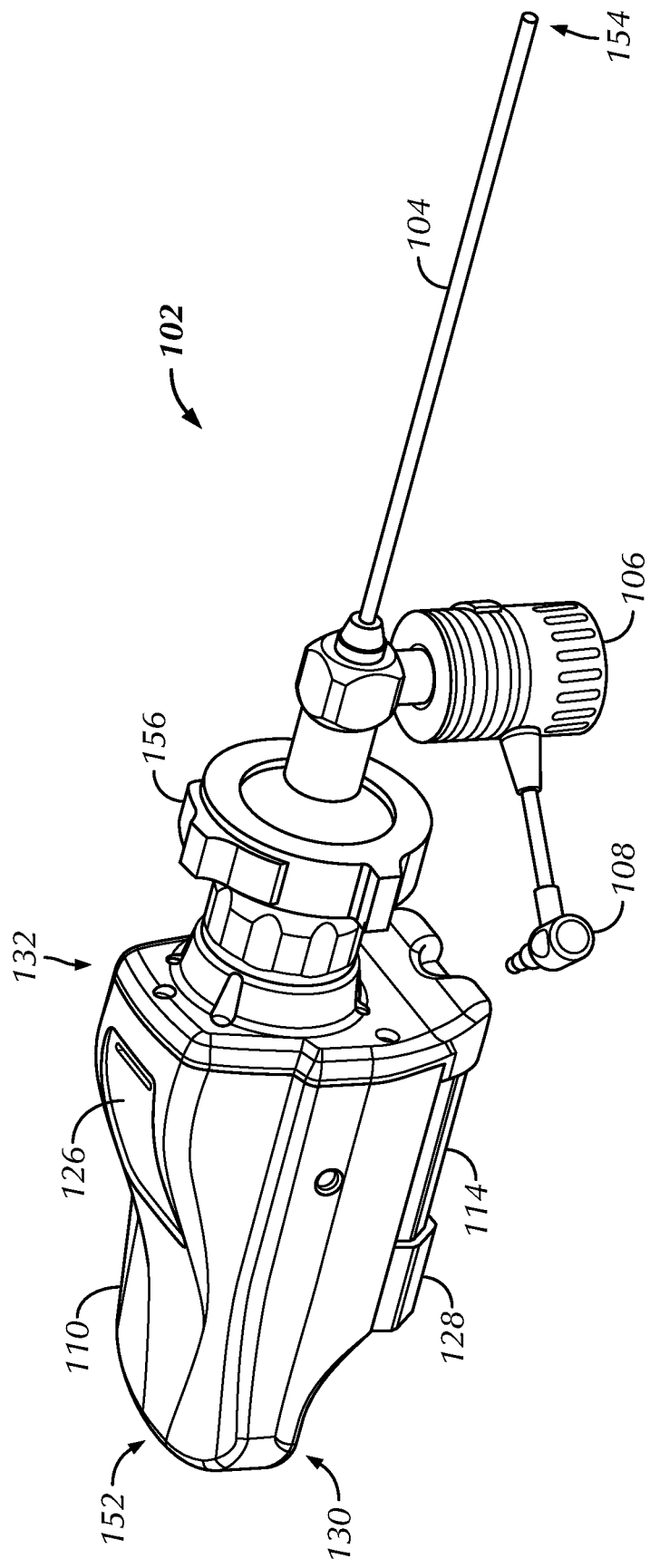
FIG. 2 is a perspective view of an endoscopic camera system, according to one embodiment.

FIG. 2 illustrates a perspective view of one embodiment of endoscopic camera system 102, including endoscope 104, light 106, cable 108, and endoscopic camera 110. In addition to the features described with regard to FIG. 1, endoscopic camera system 102 further includes a coupling 156 between endoscope 104 and endoscopic camera 110. Endoscopic camera 110 further includes a control panel 126, a battery latch 128, a tail portion 130, and a grip region 132. Endoscopic camera system 102 includes a proximal end 152 and a distal end 154. Distal end 154 may be located near the portion of endoscope 104 placed near the scene of interest. Proximal end 152 is located on an end of endoscopic camera 110.

Control panel 126 includes one or more buttons, switches, slides, dials, or other input mechanisms for controlling the operation of endoscopic camera system 102. Controls can include a power control, an illumination control, a white balance control, a zoom control, controls for wireless transmission settings, and/or other controls. Control panel 126 can also include controls for manipulating how data is displayed at monitor 164.

Battery latch 128 is a latch to hold battery 114 in place. Battery latch 128 may cooperate with other features to hold battery 114 in place. Battery latch 128 may be slidable to facilitate release of battery 114.

Tail 130 can be a portion near proximal end 152 of endoscopic camera 110. In the illustrated embodiment, tail 130 is an elongate portion having a relatively smaller height compared to an adjacent, more distal portion of endoscopic camera 110. In one embodiment, tail 130 may begin at the end of battery latch 128, when battery latch 128 is in a closed position securing battery 114 in place. Tail 130 may be an area where wireless transmitter 116 or components thereof (e.g., an antenna) are located.

Grip region 132 is a region of endoscopic camera system 102 adapted to be held by a user. Grip region 132 may configured to provide an ergonomic location for use of endoscopic camera system 102. In one embodiment, grip region 132 is located at or near a balance point of endoscopic camera system 102 to facilitate manipulation of endoscopic camera system 102 by a user. Grip region 132 may also be configured at a portion of endoscopic camera 110 that is a particular distance away from wireless transmitter 116. Designing camera 110 to position grip region 132 as far away as practicable from transmitter 116 may be advantageous, in that this configuration prevents the user's hand from interfering with data transmission from transmitter 116. For example, in the embodiment shown and other alternative embodiments, the grip region 132 may be located more than 5 centimeters, away from wireless transmitter 116. Grip region 132 may include one or more features to facilitate holding by the user, including but not limited to those described below, in reference to FIGS. 3-5.

Figure 3:
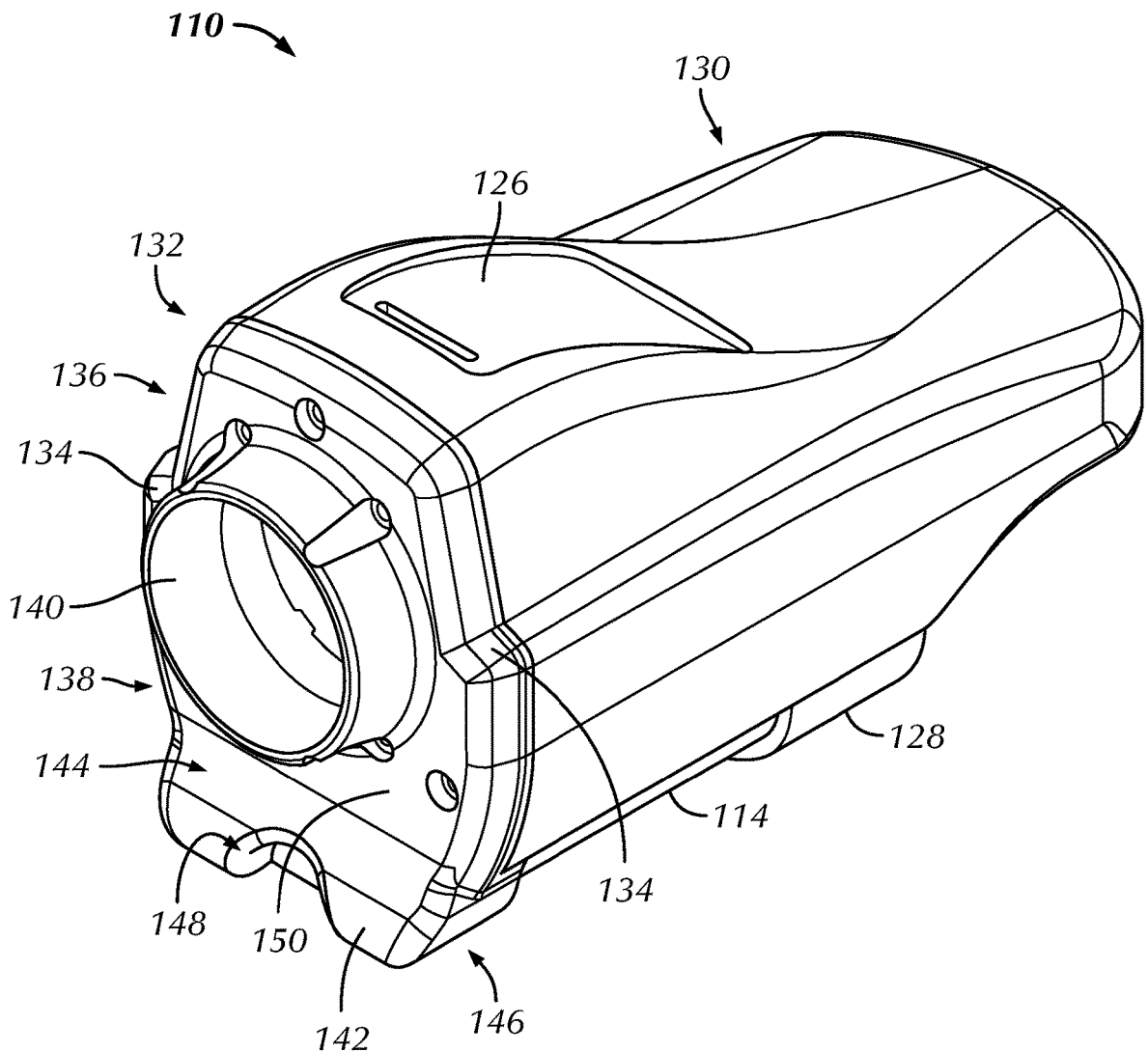
FIG. 3 is a perspective view of an endoscopic camera, according to one embodiment.
Figure 5:
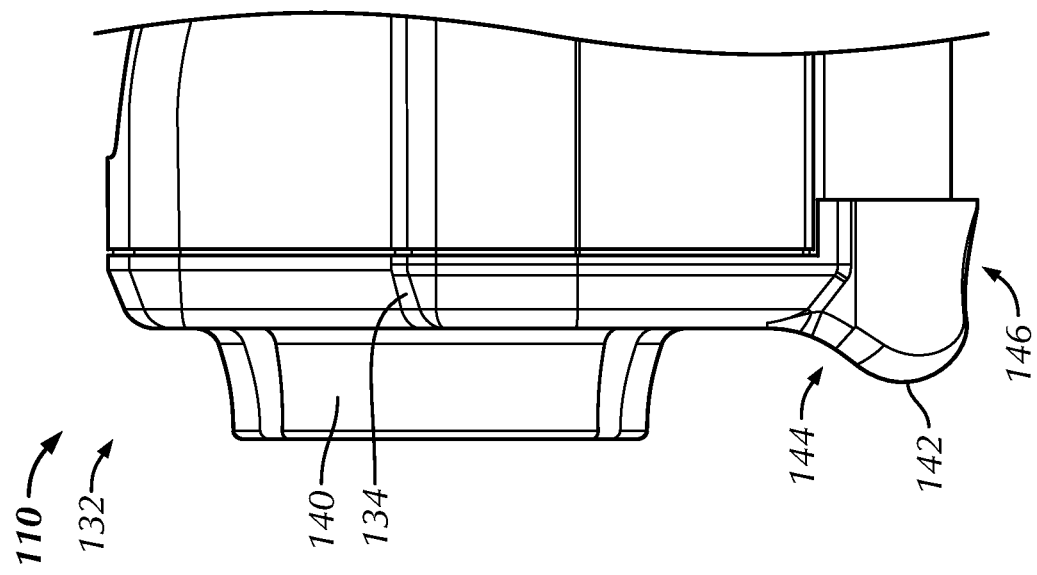
FIG. 5 is a side view of a grip region of the endoscopic camera of FIG. 3.
Figure 4:
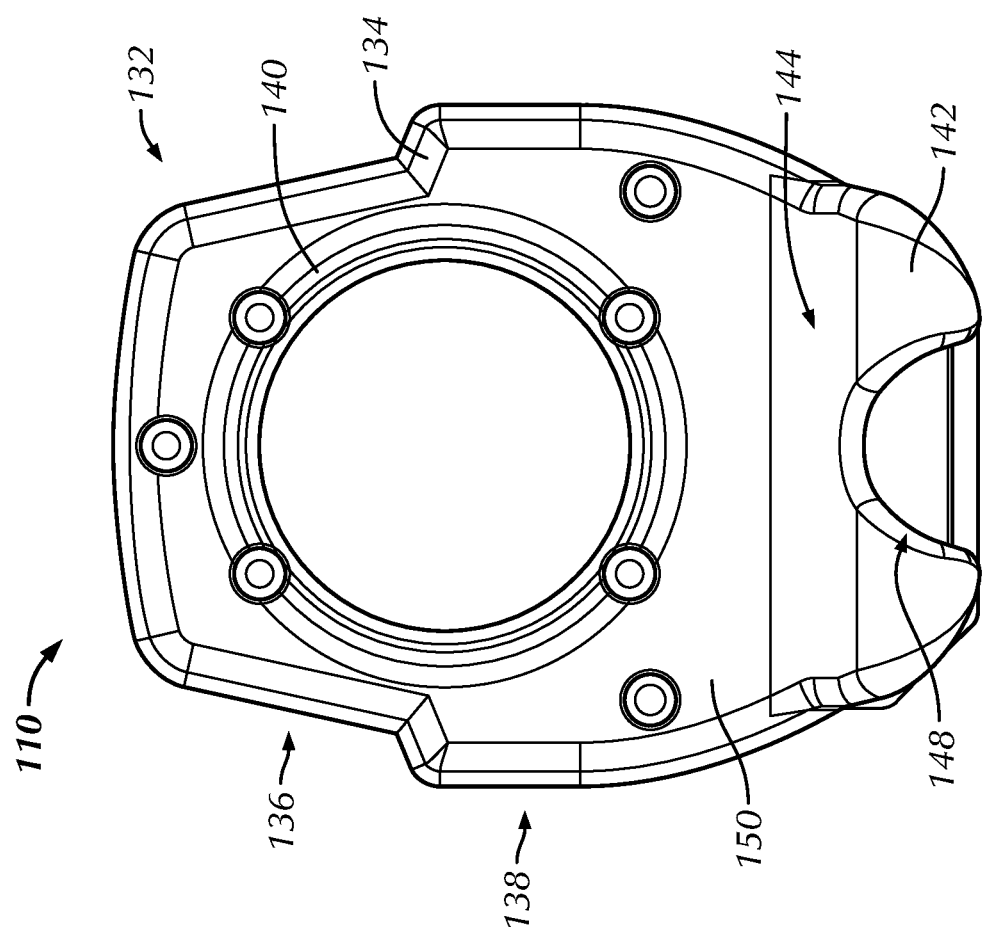
FIG. 4 is a front view of a grip region of the endoscopic camera of FIG. 3.

FIG. 3 illustrates a perspective view of endoscopic camera 110, according to one embodiment. FIG. 4 illustrates a front view of grip region 132 of endoscopic camera 110 of FIG. 3. FIG. 5 illustrates a side view of a distal end of endoscopic camera 110 of FIG. 3. In these views, endoscopic camera 110 is presented without endoscope 104, light 106, cable 108, and coupling 156 of endoscopic camera system 102 to improve visibility of grip region 132 and other portions of endoscopic camera 110. Illustrated features include shoulders 134, which divide endoscopic camera 110 into a head portion 136 and a body portion 138. Illustrated features further include an attachment collar 140, a ledge 142, a first concavity 144, a second concavity 146, a divot 148, and a face 150.

Shoulders 134 are an area of reduced width of endoscopic camera 110. In the illustrated example, shoulders 134 are located at approximately two-thirds of the way up the height of endoscopic camera 110 from the bottom of endoscopic camera 110, and shoulders 134 are an area having a width reduced by approximately fifteen percent. Shoulders 134 can provide a region to facilitate holding endoscopic camera 110. For example, a user may grip endoscopic camera 110 with one or more fingers or another part of the hand against or along one or both shoulders 134. In one embodiment, one or more of the user's fingers may be positioned substantially perpendicular to or parallel with one or both of shoulders 134. Endoscopic camera system 102 can be gripped by the user in a manner such that shoulders 134 resist unwanted rotation of endoscopic camera 110 relative to the user's hand. Shoulders 134 can further facilitate user-desired rotation of endoscopic camera 110 about the axis relative to the user's hand. Shoulders 134 can continue along a portion of the length of endoscopic camera 110 and continue along or be incorporated into tail 130.

Shoulders 134 can divide endoscopic camera 110 into head 136 and body 138. Head 136 can be defined by a portion above shoulders 134 and/or body 138. In the illustrated example, head 136 extends above shoulders 134 and has a width decreasing from shoulders 134 to the top of head 136. The top of head 136 can include a curve configured to match a curve of a user's hand to facilitate placing the user's hand or a portion thereof on the top of head 136. The height of head 136 decreases along the length of endoscopic camera 110, such that head 136 forms a slope towards and/or into tail 130. Control panel 126 is disposed on the slope of head 136. Body 138 can be described as a portion below shoulders 134 and/or head 136. In the illustrated example, body 138 has a greater width than head 136 and the width of body 138 decreases towards ledge 142.

Face 150 can be a region located at the distal end of endoscopic camera 110. Face 150 can be located within grip region 132 and may be substantially flat enough to facilitate use of grip region 132. For example, the user may wrap one or more fingers around attachment collar 140 and have a portion of the hand against face 150. In certain grips, face 150 can also be a portion of endoscopic camera 110 where a portion of the weight of endoscopic camera 110 rests against the user's hand and prevents unwanted distal movement of endoscopic camera 110 through the hand (see, e.g., FIG. 9 and FIG. 10).

Attachment collar 140 is a location at or by which endoscopic camera 110 can be coupled to coupling 156. Attachment collar 140 can be a circular protrusion extending from endoscopic camera 110. Attachment collar 140 can take other forms, such as an opening in endoscopic camera 110 into which coupling 156 can be attached. In one embodiment, attachment collar 140 is a circular protrusion from face 150 in grip region 132. Attachment collar 140 can be positioned substantially centered along the width of endoscopic camera 110 and positioned with its center substantially aligned with shoulders 134. In this manner, grip region 132 may facilitate gripping of endoscopic camera 110 using shoulders 134 and attachment collar 140.

In addition to providing attachment functionality, attachment collar 140 can be located within grip region 132 and facilitate user's holding of endoscopic camera system 102. For example, attachment collar 140 can be located within grip region 132 and provide an area around which the user may grip to hold endoscopic camera system 102. In such a position, the user may grip attachment collar 140, coupling 156, or combinations thereof. Attachment collar 140 and coupling 156 may include features to facilitate holding, such as knurling.

Ledge 142 is a protrusion from endoscopic camera 110 and can form a portion of grip region 132. Ledge 142 provides a region to facilitate holding endoscopic camera 110. For example, a user may grip endoscopic camera 110 with one or more fingers or another part of the hand against or along ledge 142. Endoscopic camera system 102 can be gripped by the user in a manner that ledge 142 resists unwanted distal or proximal motion of endoscopic camera 110 relative to the user's hand and to facilitate desired distal or proximal motion of endoscopic camera 110. In one embodiment, ledge 142 extends distally from face 150 and decreases in width as ledge 142 extends from face 150.

Ledge 142 can include one or more features, such as a first concavity 144, a second concavity 146, and a divot 148. First concavity 144 and second concavity 146 can run along ledge 142, be separated by a convex portion of ledge 142, and provide a location for the user to place fingers or a portion of the user's hand to improve grip on ledge 142 or to facilitate control of endoscopic camera system 102 as a whole. Divot 148 can be a concave space in ledge 142. Divot 148 can be a grip enhancing feature. For example, divot 148 can be a place at which the user may place a portion of the user's hand. Divot 148 can be adapted to provide a channel or other opening through which battery 114 may be manipulated. For example, ledge 142 can cooperate with battery latch 128 to hold battery 114 in place. Battery 114 can be located proximal to ledge 142, and divot 148 can provide a channel through which the user can manipulate battery 114 to insert or remove battery 114.

Grip region 132 can be configured to encourage or discourage a user to hold endoscopic camera system 102 in a particular way or location. For example, grip region 132 can be located to encourage a user to hold endoscopic camera system 102 a particular distance away from wireless transmitter 116, such as 5 centimeters or more. Grip region 132 can be located to encourage a user to grab endoscopic camera system 102 a particular distance away from a balance point of endoscopic camera system 102, a particular distance away from wireless transmitter 116, or a combination thereof. For example, endoscopic camera system 102 can be configured to have a balance point near grip region 132. The balance point can be located more than 5 centimeters away from wireless transmitter 116.

Grip region 132 can be configured to provide multiple, complimentary features to facilitate grip. For example, grip region 132 can be configured for a user to grip attachment collar 140 to control rotational movement of endoscopic camera system 102 relative to the user's hand. Grip region 132 can be further configured for a user to rest a portion of the user's hand or fingers within first concavity 144 to control proximal and distal movement of endoscopic camera system 102.

Figures 6, 7:
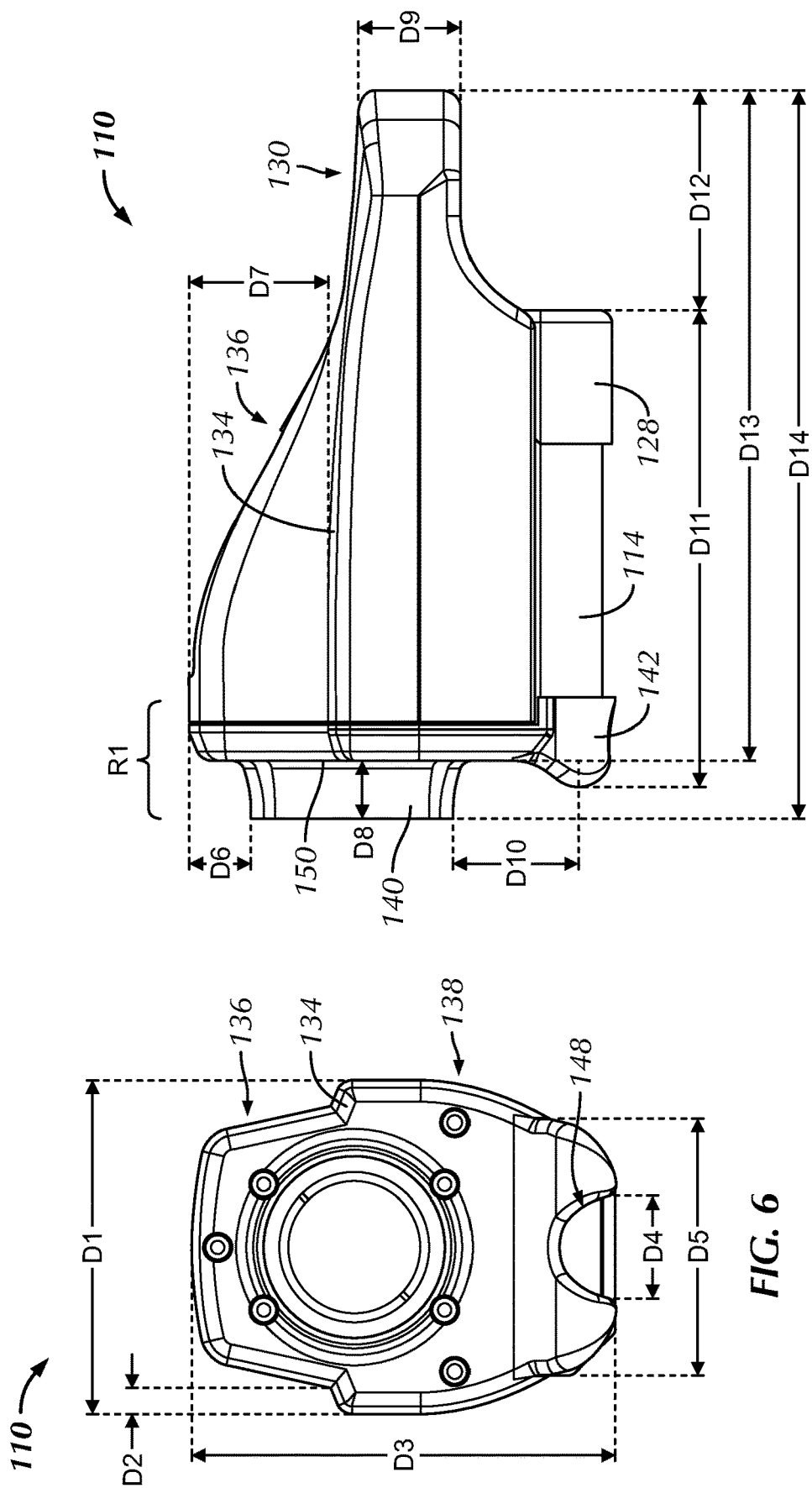
FIG. 6 illustrates a front view of the endoscopic camera with labels showing example sizes of various components and portions, according to one embodiment.
FIG. 7 illustrates a side view of the endoscopic camera with labels showing example sizes of various components and portions, according to one embodiment.

FIGS. 6 and 7 are front and side views, respectively, of endoscopic camera 110, with labels illustrating dimensions of the various components and portions of endoscopic camera 110, according to one embodiment. The dimensions are meant to be exemplary in nature, applying to one embodiment, and any or all the dimensions may vary in alternative embodiments. Additionally, each exemplary dimension listed below may vary slightly, for example by approximately +/−0.1 inch, without departing from the scope of the invention. Therefore, the dimensions listed below should be interpreted as examples only and should not be interpreted as limiting the scope of the invention as it is set forth in the claims.

FIG. 6 illustrates example dimensions D1, D2, D3, D4, and D5. Distance D1 is the width of the widest portion of endoscopic camera 110. In the illustrated embodiment, distance D1 is also the width of endoscopic camera 110 measured as shoulders 134 begin. In one embodiment, distance D1 is approximately 2.20 inches. In various alternative embodiments D1 may be between about 1.10 inches and about 3.30 inches, or more ideally between about 1.54 inches and about 2.86 inches, or even more ideally between about 1.98 inches and about 2.42 inches. Distance D2 is the width of one shoulder 134, or in other words a narrowing of the width of endoscopic camera 110 at each shoulder 134. In one embodiment, distance D2 is approximately inches. In various alternative embodiments D2 may be between about 0.09 inches and about inches, or more ideally between about 0.13 inches and about 0.23 inches, or even more ideally between about 0.16 inches and about 0.20 inches. Distance D3 is the height of endoscopic camera 110 measured from a bottom of ledge 142 to a top of head 136. In one embodiment, distance D3 is approximately 2.79 inches. In various alternative embodiments D3 may be between about 1.40 inches and about 4.19 inches, or more ideally between about 1.96 inches and about 3.63 inches, or even more ideally between about 2.5 inches and about 3.07 inches. Distance D4 is the width of the widest part of divot 148. In one embodiment, distance D4 is approximately 0.68 inches. In various alternative embodiments D4 may be between about 0.34 inches and about 1.02 inches, or more ideally between about 0.48 inches and about 0.88 inches, or even more ideally between about 0.61 inches and about 0.75 inches. Distance D5 is the width of the widest part of ledge 142. In one embodiment, distance D5 is approximately 1.68 inches. In various alternative embodiments D5 may be between about 0.84 inches and about 2.52 inches, or more ideally between about 1.18 inches and about 2.18 inches, or even more ideally between about 1.51 inches and about 1.85 inches.

FIG. 7 illustrates example dimensions D6, D7, D8, D9, D10, D11, D12, D13, and D14 and region R1. Distance D6 is the distance from a top portion of attachment collar 140 to the top of endoscopic camera 110 (e.g., top of head 136). In one embodiment, distance D6 is approximately 0.40 inches. In various alternative embodiments D6 may be between about 0.20 inches and about 0.60 inches, or more ideally between about 0.28 inches and about 0.52 inches, or even more ideally between about 0.36 inches and about 0.44 inches. Distance D7 is the distance from a top of shoulders 134 to the top of endoscopic camera 110 (e.g., top of head 136). In one embodiment, distance D7 is approximately 0.90 inches. In various alternative embodiments D7 may be between about 0.45 inches and about 1.35 inches, or more ideally between about 0.63 inches and about 1.17 inches, or even more ideally between about 0.81 inches and about 0.99 inches. Distance D8 is the distance that attachment collar 140 extends from face 150 of grip region 132. In one embodiment, distance D8 is approximately 0.38 inches. In various alternative embodiments D8 may be between about 0.19 inches and about 0.57 inches, or more ideally between about 0.27 inches and about 0.49 inches, or even more ideally between about 0.34 inches and about 0.42 inches. Distance D9 is the height of tail 130. In one embodiment, distance D9 is approximately 0.66 inches. In various alternative embodiments D9 may be between about 0.33 inches and about 0.99 inches, or more ideally between about 0.46 inches and about 0.86 inches, or even more ideally between about 0.59 inches and about 0.73 inches. Distance D10 is the distance from the bottom of attachment collar 140 to a middle of ledge 142. In one embodiment, distance D10 is approximately 0.81 inches. In various alternative embodiments D10 may be between about 0.41 inches and about 1.22 inches, or more ideally between about 0.57 inches and about 1.05 inches, or even more ideally between about 0.73 inches and about 0.89 inches. Distance D11 is the distance from the distal end of ledge 142 to the proximal end of battery latch 128. In one embodiment, distance D11 is approximately 3.17 inches. In various alternative embodiments D11 may be between about 1.59 inches and about 4.76 inches, or more ideally between about 2.22 inches and about 4.12 inches, or even more ideally between about 2.85 inches and about 3.49 inches. Distance D12 is the distance the proximal end of battery latch 128 to the proximal end of tail 130. This can also be described as the width of tail 130. In one embodiment, distance D12 is approximately 1.44 inches. In various alternative embodiments D12 may be between about 0.72 inches and about 2.16 inches, or more ideally between about 1.01 inches and about 1.87 inches, or even more ideally between about 1.30 inches and about 1.58 inches. Distance D13 is the distance from face 150 to the proximal end of tail 130. In one embodiment, distance D13 is approximately 4.43 inches. In various alternative embodiments D13 may be between about 2.22 inches and about 6.65 inches, or more ideally between about 3.10 inches and about 5.76 inches, or even more ideally between about 3.99 inches and about 4.87 inches. Distance D14 is the distance from the distal end of attachment collar 140 to the proximal end of tail 130. In one embodiment, distance D14 is approximately 4.80 inches. In various alternative embodiments D14 may be between about 2.40 inches and about 7.20 inches, or more ideally between about 3.36 inches and about 6.24 inches, or even more ideally between about 4.32 inches and about 5.28 inches. In one embodiment, region R1 is the region in which the balance point of endoscopic camera system 102 is located. The region R1 is approximately centered at face 150.

Figure 8:
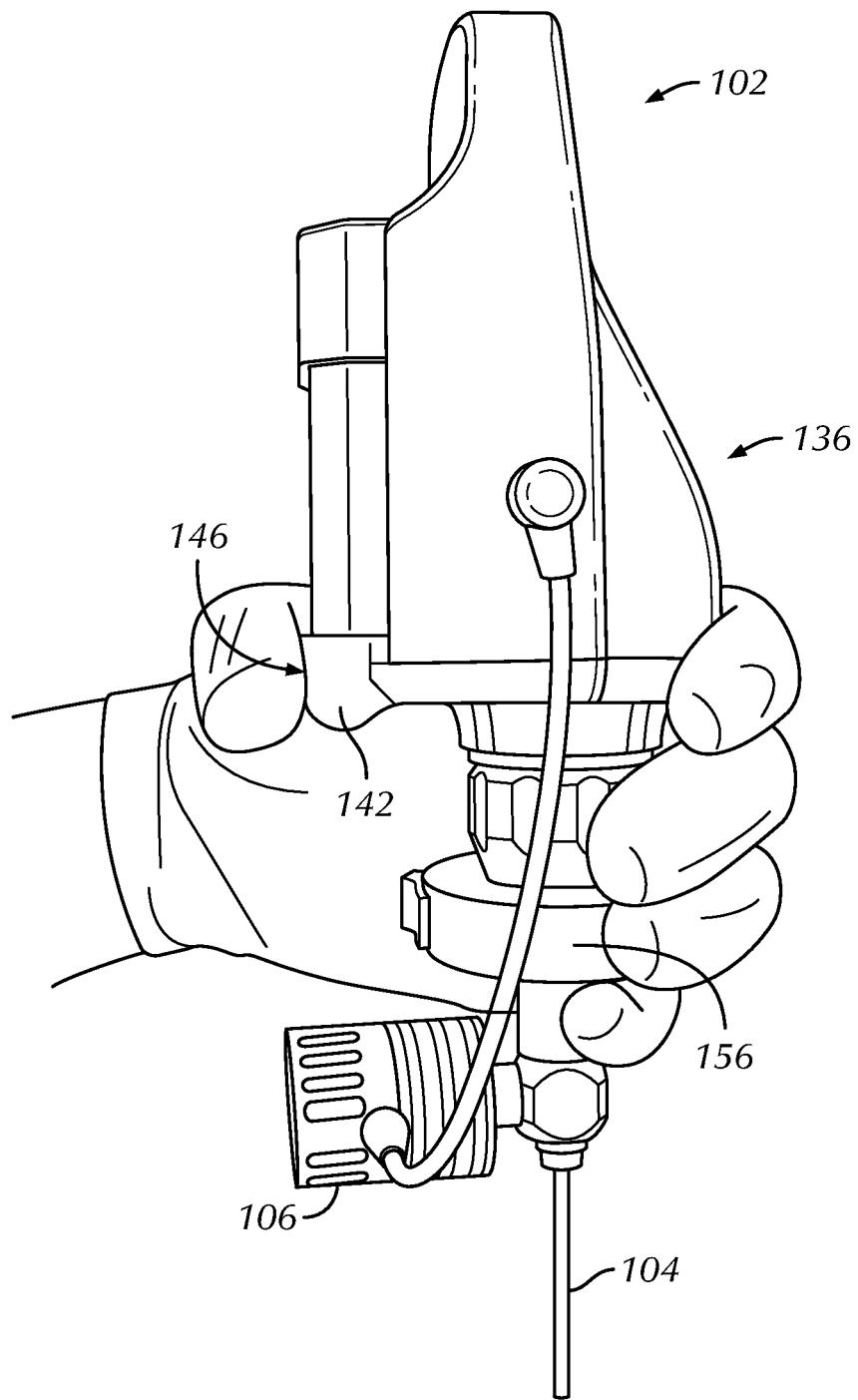
FIG. 8 illustrates a first example grip on an endoscopic camera, according to one embodiment.

FIG. 8 illustrates a method for gripping endoscopic camera system 102, according to one embodiment. In this embodiment, the user's thumb is placed against ledge 142 with a portion of the thumb in second concavity 146. The user's index finger is placed on top of head 136, and the index finger may rest on a curve of head 136 configured to receive a portion of a user's hand. The remaining fingers are placed against coupling 156.

Figure 9:
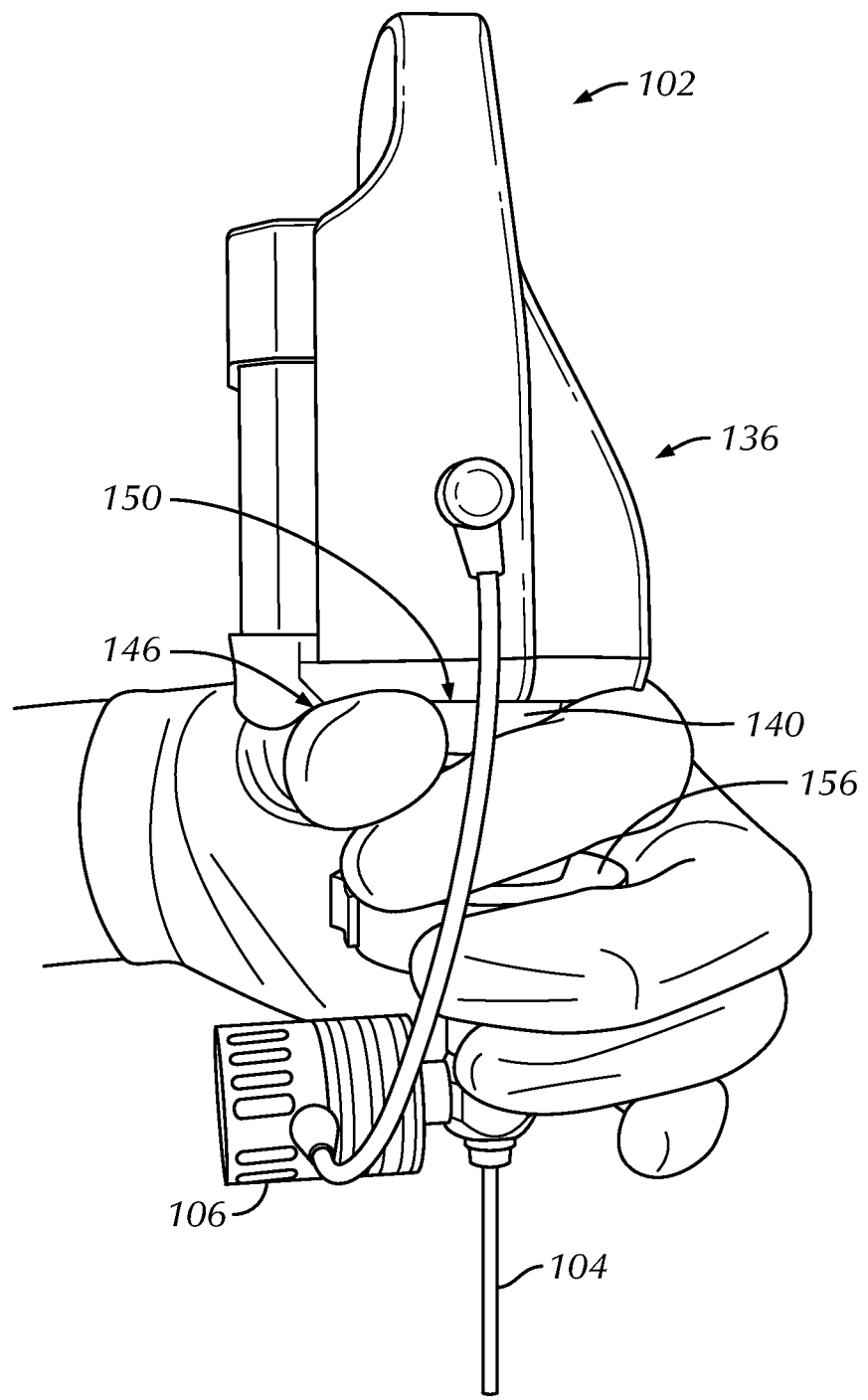
FIG. 9 illustrates a second example grip on an endoscopic camera, according to one embodiment.

FIG. 9 illustrates an alternative embodiment of a method for gripping endoscopic camera system 102. In this embodiment, the user's thumb is placed against, and at least partially within, first concavity 144 in ledge 142. The user's thumb is also placed against face 150. The user's index finger is wrapped partially around attachment collar 140 with a portion of the finger resting against face 150 and with the end of the finger resting against coupling 156. The user's index finger and thumb may at least partially support the weight of endoscopic camera system 102 where face 150 meets the user's index finger and thumb and where first concavity 144 meets the user's thumb. The user's remaining fingers are also placed against coupling 156. These fingers may provide additional control of and support for endoscopic camera system 102.

Figure 10:
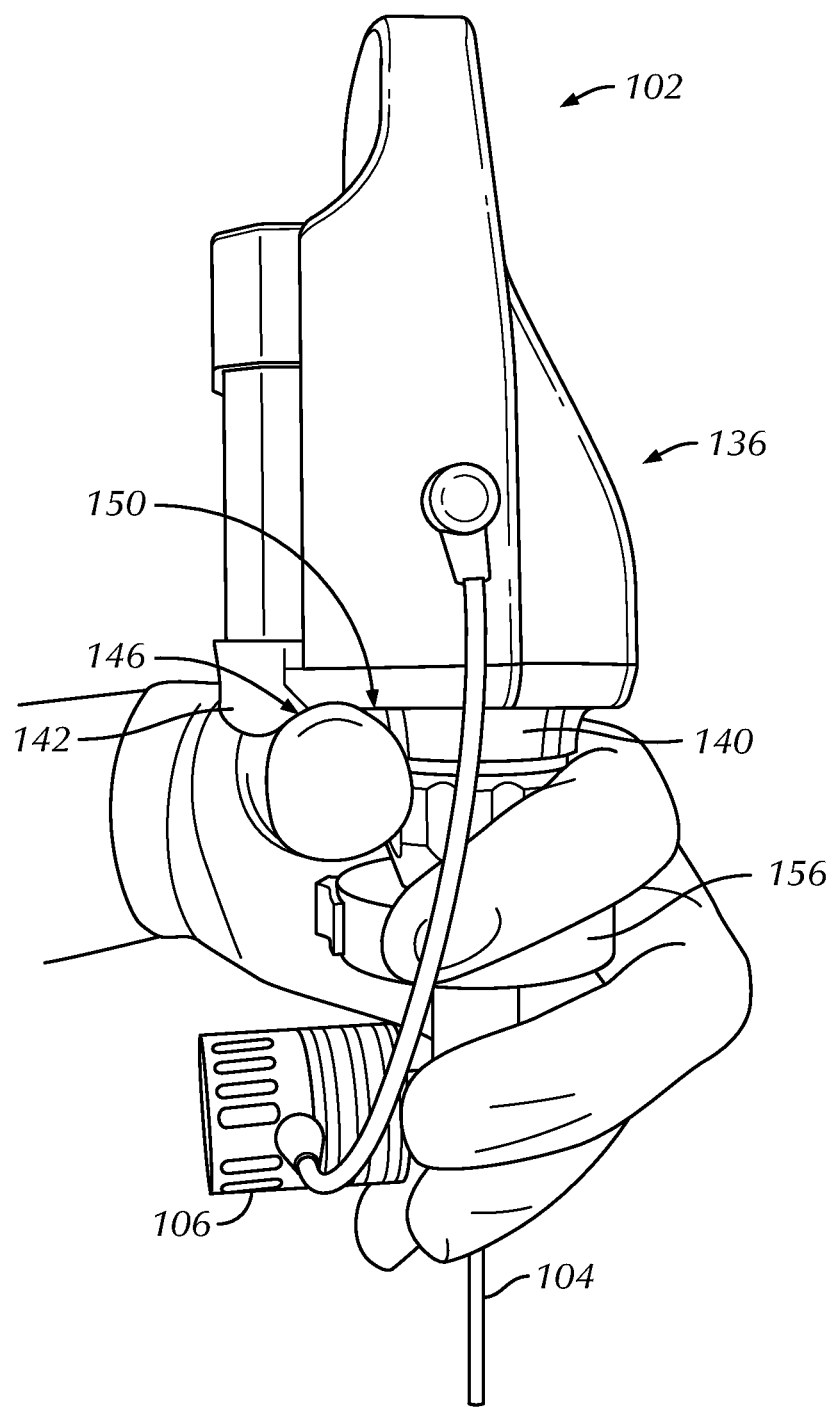
FIG. 10 illustrates a third example grip on an endoscopic camera, according to one embodiment.

FIG. 10 illustrates another alternative embodiment of a method for gripping an endoscopic camera system 102. In this example, the user's thumb is placed against, and at least partially within, first concavity 144 in ledge 142. The user's thumb is also placed against face 150. The user's thumb may at least partially support the weight of endoscopic camera system 102 where the thumb contacts first concavity 144 and face 150. The user's index finger is wrapped partially around attachment collar 140 and coupling 156, with the end of the finger resting against coupling 156. The user's remaining fingers are draped along coupling 156 and endoscope 104 with some of the ends of the fingers resting against light 106.

Figure 11:
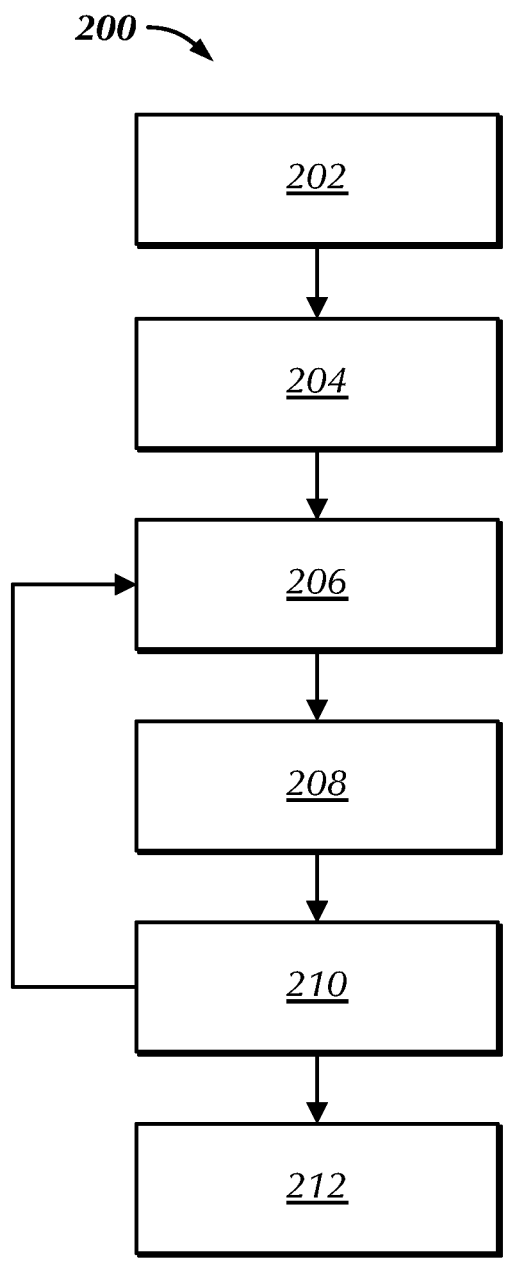
FIG. 11 illustrates a process for visualizing a scene of interest with an endoscopic camera system, according to one embodiment.

FIG. 11 illustrates one embodiment of a method 200 for visualizing a scene of interest with an endoscope by modulating illumination output to correct for overexposure or underexposure. In certain methods for visualizing a scene of interest, video capture parameters, such as exposure time or sensor gain, may be the primary parameters modified to adjust exposure of an image while maintaining constant illumination of the scene. In other methods, illumination output of a light may be the primary parameter modified to affect exposure of video, while video capture parameters affecting exposure remain substantially constant. Advantageously, modifying the illumination can be used to improve battery life of the system and decrease heat output. This can be done by, for example, keeping video capture parameters affecting exposure at a relatively high setting (e.g., settings tending to cause overexposure), which allows for illumination output to be relatively reduced. Reduced illumination output can beneficially reduce battery draw and heat output for the illumination source. With exposure parameters at a relatively high setting, less illumination is needed to properly expose the scene than would be required if the video capture parameters were reduced.

According to the embodiment depicted in FIG. 11, the method 200 may start by advancing the distal end of an endoscopic camera system to a scene of interest 202. Next, the endoscopic camera system may be used to illuminate the scene of interest 204. A video signal can then be captured by the system 206, and a processor of the system may be used to determine exposure of the video signal 208. If the processor determines that the video signal is overexposed or underexposed, it can then send a signal to change the illumination output from the light source 210. The method may then continue by removing the endoscopic camera system 212 or by continuing capturing video using the changed illumination output 206.

Prior to block 202, the process 200 can include various preparatory steps, including but not limited to selecting components of endoscopic camera system 102 (e.g., endoscope 104, light 106, and endoscopic camera 110), assembling endoscopic camera system 102 (e.g., optically connecting endoscope 104 to endoscopic camera 110 via coupling 156), establishing communication between wireless transmitter 116 and receiver 162, calibrating endoscopic camera system 102 and monitor 164, sterilizing endoscopic camera system 102, preparing the subject for the procedure, or other preparatory steps.

Block 202 recites "advancing distal end to scene of interest." In an endoscopic procedure, the user can advance distal end 154 of endoscopic camera system 102 toward a scene of interest. For example, process 200 can be used for visualizing a scene of interest during a procedure in a subject's sinus cavity, and the distal end of endoscopic camera system 102 can be advanced through subject's nostril or an access hole in subject's gingival tissue towards subject's sinus cavity.

Block 204 recites "illuminating scene of interest." With distal end 154 located near the scene of interest, light 106 can be used to provide illumination at the scene of interest. For example, light 106 can shine into a proximal end of endoscope 104, and endoscope 104 transmits the light down the length of the scope and out distal end 154 to illuminate the scene of interest. This illumination can be used to facilitate the capture of video information using endoscopic camera system 102.

The illumination can be provided according to various parameters. Light 106 can provide illumination at a particular illumination output that can be varied (e.g., measured in lumens) manually by the user, automatically by the endoscopic camera 110 (e.g., by providing a signal through cable 108), or combinations thereof. In some examples, output of light 106 is controlled by pulse width modulation of a signal. For example, the duty cycle can be varied to increase or decrease the output of light 106.

Block 206 recites "capturing video." Visual information at distal end 154 can travel down endoscope 104 and received at camera 112 in endoscopic camera 110. Camera 112 can convert the visual information into electrical signals. These signals can be transmitted to receiver 162 for display at monitor 164. The signals may undergo processing at camera 112, endoscopic camera 110, or elsewhere. The processing can include white balancing, filtering, noise reduction, level adjustments, color adjustments, compression, and other processing.

Camera 112 may operate according to particular parameters, for example camera 112 can operate according to video capture characteristics that affect exposure of the resulting video. These characteristics can include, but need not be limited to shutter speed, exposure time, and imaging sensor sensitivity to light. These characteristics can be preset to maximize exposure of the resulting video, such as by decreasing shutter speed, increasing exposure time, and increasing imaging sensor sensitivity. Other parameters can include resolution, compression, frame rate, white balance, and other parameters.

Block 208 recites "determining exposure." The signal from camera 112 can be analyzed to determine the exposure of one or more frames of the video image. This analysis can be performed within camera 112, on processing unit 118 or elsewhere. In one embodiment, this analysis can be performed by measuring a distribution of the brightness value of pixels that make up one or more video frames. Responsive to a first threshold number of pixels being within a threshold region, the image may be determined to be improperly exposed. In another example, this analysis can be performed by averaging the pixel value in one or more frames and determining whether the resulting value is past an overexposure or underexposure threshold. In yet another example, the brightness may be determined based on received input from the user (e.g., the user pushes an "increase brightness" button, which may indicate that the video is underexposed). The result of block 208 may be a determination whether one or more frames of a video signal are underexposed, properly exposed, or overexposed. Another result may be a measurement of how overexposed or underexposed the one or more frames are.

Block 210 recites "changing illumination output." Responsive to the video signal being underexposed or overexposed, the illumination output can be modified. For example, if the video signal is underexposed, the illumination output can be increased to bring the signal to proper exposure. If the video signal is overexposed, the illumination output can be decreased to bring the signal to proper exposure. Changing illumination output can be performed instead of or in addition to changing camera settings. For example, the exposure may be corrected by maintaining the same video capture characteristics that produced the overexposed or underexposed frame and changing the illumination output of light 106. The amount by which illumination output is changed can depend on various parameters, including whether illumination output is the only variable being changed, an amount of exposure or underexposure, whether previous frames were also overexposed or underexposed, and/or other parameters.

Changing illumination output may be limited, to avoid potentially undesirable rapid changing of illumination. In one embodiment, illumination output is changed responsive to a threshold number of frames being improperly exposed. For instance, the illumination output is increased after 12 frames being underexposed. In another example, changes to illumination output may be capped at a certain number of frames (e.g., illumination output cannot be changed more than once every 24 frames).

The process of capturing video, determining exposure, and changing illumination output in blocks 206, 208, and 210 may repeat until, for example, the user intervenes (e.g., by turning off video capture at the completion of the procedure).

Block 212 recites "removing endoscope." The process 200 can conclude with endoscopic camera system 102 being removed from the scene of interest and the subject, such as at the completion of the procedure.

With regard to the processes, systems, methods, and other disclosures herein, although the steps of such processes, etc. have been described as occurring according to a certain ordered sequence, such processes could be practiced with the described steps performed in an order other than the order described herein. Additionally, in various embodiments, certain steps could be performed simultaneously, other steps could be added, and/or certain steps described herein could be omitted. In other words, the descriptions of processes herein are provided for the purpose of illustrating certain examples, and should in no way be construed so as to limit the claims.

Accordingly, the above description is intended to be illustrative and not restrictive. Many examples and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future examples. In sum, the application is capable of modification and variation.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may have such instructions stored on computer readable media for carrying out the functions described herein.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

In the foregoing Detailed Description, various features are grouped together in various examples for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter. While embodiments of the present invention have been shown and described, various modifications may be made without departing from the scope of the present invention. The invention, therefore, should not be limited, except to the following claims, and their equivalents.

The invention claimed is:

1. A wireless endoscopic camera, comprising:
   a grip region at a distal end of the wireless endoscopic camera, wherein the grip region comprises an attachment collar that is configured to couple the wireless endoscopic camera to an endoscope; and
   a wireless transmitter located nearer to a proximal end of the wireless endoscopic camera than the distal end,
   wherein, when the wireless endoscopic camera and the endoscope are coupled to each other, a balance point of the wireless endoscopic camera and the endoscope is located at the grip region.

2. The wireless endoscopic camera of claim 1, wherein, along a distal direction, the attachment collar tapers inwardly.

3. The wireless endoscopic camera of claim 2, wherein, along the distal direction, a cross-sectional shape of the attachment collar is a circle.

4. The wireless endoscopic camera of claim 1, wherein the attachment collar is centered along a width of the wireless endoscopic camera, and
   wherein the width of the wireless endoscopic camera extends along a dimension that is perpendicular to a longitudinal axis of the endoscope when the endoscope is coupled to the wireless endoscopic camera.

5. The wireless endoscopic camera of claim 1, further comprising a processing unit that is configured to control (i) the wireless transmitter and (ii) a light source,
   wherein the light source is external and communicatively couplable to the wireless endoscopic camera.

6. The wireless endoscopic camera of claim 5, further comprising a battery that is configured to electrically couple to the wireless transmitter and the light source.

7. The wireless endoscopic camera of claim 6, wherein the battery is configured to removably couple with the wireless endoscopic camera.

8. The wireless endoscopic camera of claim 6, wherein the battery is a rechargeable battery that is integrated into the wireless endoscopic camera.

9. The wireless endoscopic camera of claim 1, further comprising a cable port on an external surface of the wireless endoscopic camera,
   wherein the cable port is configured to receive a cable for communicatively coupling the wireless endoscopic camera to a light source.

10. The wireless endoscopic camera of claim 9, wherein the cable port is located proximal of the grip region.

11. The wireless endoscopic camera of claim 9, wherein the cable port is configured to electrically couple the light source to a battery of the wireless endoscopic camera.

12. The wireless endoscopic camera of claim 1, further comprising a control panel disposed on the wireless endoscopic camera proximal to the grip region, wherein the control panel comprises a plurality of input mechanisms for controlling operation of the wireless endoscopic camera.

13. A wireless endoscopic camera system, comprising:
   an endoscopic camera, comprising:
      a grip region at a distal end of the endoscopic camera, the grip region comprising an attachment collar that is configured to couple the endoscopic camera to an endoscope,
      a wireless transmitter located nearer to a proximal end of the endoscopic camera than the distal end, and
      a cable port on an external surface of the endoscopic camera; and a cable that is configured to couple, via the cable port, a light source to at least one of component of the endoscopic camera selected from a group consisting of: (i) a processing unit and (ii) a battery.

14. The wireless endoscopic camera system of claim 13, further comprising the battery and the light source,
wherein the cable couples the light source to the battery of the endoscopic camera.

15. The wireless endoscopic camera system of claim 14, further comprising the processing unit,
wherein the battery electrically powers the light source, the processing unit, and the wireless transmitter.

16. The wireless endoscopic camera system of claim 15, wherein the cable couples the light source to the processing unit of the endoscopic camera, and
wherein the processing unit is configured to control (i) the wireless transmitter and (ii) the light source.

17. The wireless endoscopic camera system of claim 13, wherein the cable port is proximal of the grip region.

18. The wireless endoscopic camera system of claim 13, wherein the light source comprises a cylindrical canister with a port for attaching to the endoscope.

19. The wireless endoscopic camera system of claim 18, further comprising the endoscope, wherein the endoscope comprises a post for coupling to the port of the light source.

20. The wireless endoscopic camera system of claim 13, wherein, along a distal direction, the attachment collar tapers inwardly.

\* \* \* \* \*